(12) United States Patent
Klotzkin

(10) Patent No.: US 8,729,502 B1
(45) Date of Patent: May 20, 2014

(54) SIMULTANEOUS, SINGLE-DETECTOR FLUORESCENCE DETECTION OF MULTIPLE ANALYTES WITH FREQUENCY-SPECIFIC LOCK-IN DETECTION

(75) Inventor: David Klotzkin, Vestal, NY (US)

(73) Assignee: The Research Foundation for The State University of New York, Binghamton, NY (US)

( * ) Notice: Subject to any disclaimer, the term of this patent is extended or adjusted under 35 U.S.C. 154(b) by 180 days.

(21) Appl. No.: 13/279,083

(22) Filed: Oct. 21, 2011

Related U.S. Application Data

(60) Provisional application No. 61/407,887, filed on Oct. 28, 2010.

(51) Int. Cl.
G01N 21/64 (2006.01)
(52) U.S. Cl.
USPC .................................. 250/458.1; 250/459.1
(58) Field of Classification Search
USPC .......................................... 250/458.1, 459.1
See application file for complete search history.

(56) References Cited

U.S. PATENT DOCUMENTS

| | | | |
|---|---|---|---|
| 5,208,651 A * | 5/1993 | Buican | 356/451 |
| 5,603,351 A | 2/1997 | Cherukuri et al. | |
| 5,784,157 A | 7/1998 | Gorfinkel et al. | |
| 5,784,162 A | 7/1998 | Cabib et al. | |
| 5,817,462 A | 10/1998 | Garini et al. | |
| 5,835,214 A | 11/1998 | Cabib et al. | |
| 5,863,504 A | 1/1999 | Heffelfinger et al. | |
| 5,980,704 A | 11/1999 | Cherukuri et al. | |
| 6,038,023 A | 3/2000 | Carlson et al. | |
| 6,118,126 A | 9/2000 | Zanzucchi | |
| 6,287,765 B1 | 9/2001 | Cubicciotti | |
| 6,331,439 B1 | 12/2001 | Cherukuri et al. | |
| 6,379,929 B1 | 4/2002 | Burns et al. | |
| 6,403,947 B1 | 6/2002 | Hoyt et al. | |
| 6,545,739 B1 | 4/2003 | Matsumoto et al. | |
| 6,596,545 B1 | 7/2003 | Wagner et al. | |
| 6,608,360 B2 | 8/2003 | Starikov et al. | |
| 6,682,942 B1 | 1/2004 | Wagner et al. | |
| 6,685,810 B2 | 2/2004 | Noca et al. | |
| 6,686,201 B2 | 2/2004 | Potyrailo et al. | |
| 6,716,948 B1 | 4/2004 | Klaerner et al. | |
| 6,762,025 B2 | 7/2004 | Cubicciotti | |

(Continued)

OTHER PUBLICATIONS

Joseph R. Lakowicz, Principles of fluorescence spectroscopy, Springer, 2006, p. 743.

(Continued)

*Primary Examiner* — Christine Sung
(74) *Attorney, Agent, or Firm* — Steven M. Hoffberg; Ostrolenk Faber LLP

(57) ABSTRACT

Microfluidics has made great progress in integrating many aspects of biological analysis and testing into the microscale. One aspect which has proven challenging to miniaturize has been fluorescence testing, as a complete fluorescence system requires an integrated light source, detector and filters to filter out the excitation light (from the light source) from the detector. Here we demonstrate that with polarization filtering of the excitation light and multiple dye sources modulated at different frequencies, a high-sensitivity, multi-dye system with one detector can be realized. Simultaneous detection and quantition of a mixture of two different dyes is demonstrated with no physical change in the measurement setup. The degree of interaction of the dyes is measured. This system is readily adaptable to integrated lab-on-a-chip microfluorescence.

27 Claims, 5 Drawing Sheets

(56) References Cited

U.S. PATENT DOCUMENTS

| | | |
|---|---|---|
| 6,846,638 B2 | 1/2005 | Shipwash |
| 6,858,852 B2 | 2/2005 | Wolleschensky et al. |
| 6,870,612 B2 | 3/2005 | Jiang |
| 6,881,979 B2 | 4/2005 | Starikov et al. |
| 6,887,202 B2 | 5/2005 | Currie et al. |
| 6,934,435 B2 | 8/2005 | Kane |
| 6,934,836 B2 | 8/2005 | Strand et al. |
| 6,965,431 B2 | 11/2005 | Vo-Dinh et al. |
| 6,986,739 B2 | 1/2006 | Warren et al. |
| 6,995,841 B2 | 2/2006 | Scott et al. |
| 7,016,022 B2 | 3/2006 | Fritz et al. |
| 7,087,444 B2 | 8/2006 | Wong et al. |
| 7,142,303 B2 | 11/2006 | Gianchandani et al. |
| 7,163,658 B2 | 1/2007 | Bension |
| 7,215,425 B2 | 5/2007 | Rezachek et al. |
| 7,239,388 B2 | 7/2007 | Shribak et al. |
| 7,259,217 B2 | 8/2007 | Klaerner et al. |
| 7,291,564 B1 | 11/2007 | Jackson |
| 7,302,830 B2 | 12/2007 | Kolosov et al. |
| RE39,977 E | 1/2008 | Treado et al. |
| 7,336,323 B2 | 2/2008 | Wang |
| 7,362,489 B2 | 4/2008 | Wang et al. |
| 7,372,567 B2 | 5/2008 | Shribak et al. |
| 7,403,812 B2 | 7/2008 | Rice et al. |
| 7,417,796 B2 | 8/2008 | Wang |
| 7,444,053 B2 | 10/2008 | Schmidt et al. |
| 7,461,547 B2 | 12/2008 | Terabayashi et al. |
| 7,463,353 B2 | 12/2008 | Yershov |
| 7,465,382 B2 | 12/2008 | Paul et al. |
| 7,466,418 B2 | 12/2008 | Nilson et al. |
| 7,474,398 B2 | 1/2009 | Nilson et al. |
| 7,474,399 B2 | 1/2009 | Nilson et al. |
| 7,476,504 B2 | 1/2009 | Turner |
| 7,507,575 B2 | 3/2009 | Bedingham et al. |
| 7,511,811 B2 | 3/2009 | Scott et al. |
| 7,515,953 B2 | 4/2009 | Madar et al. |
| 7,525,653 B1 | 4/2009 | Hug et al. |
| 7,531,363 B2 | 5/2009 | Cole et al. |
| 7,550,069 B2 | 6/2009 | Feldman et al. |
| 7,555,332 B2 | 6/2009 | Rice et al. |
| 7,563,350 B2 | 7/2009 | Feldman et al. |
| 7,569,382 B2 | 8/2009 | Li |
| 7,586,604 B2 | 9/2009 | Sharpe et al. |
| 7,590,161 B1 | 9/2009 | Hug et al. |
| 7,598,371 B2 | 10/2009 | Willson et al. |
| 7,603,167 B2 | 10/2009 | Stearns et al. |
| 7,612,883 B2 | 11/2009 | Que et al. |
| 7,630,073 B2 | 12/2009 | Lundquist et al. |
| 7,645,596 B2 | 1/2010 | Williams et al. |
| 7,653,429 B2 | 1/2010 | Madar et al. |
| 7,659,968 B2 | 2/2010 | Wang et al. |
| 7,691,244 B2 | 4/2010 | Levitan et al. |
| 7,692,783 B2 | 4/2010 | Lundquist et al. |
| 7,708,873 B2 | 5/2010 | Bazant et al. |
| 7,709,249 B2 | 5/2010 | Bedingham et al. |
| 7,715,001 B2 | 5/2010 | Lundquist et al. |
| 7,722,753 B2 | 5/2010 | Yamamoto |
| 7,723,116 B2 | 5/2010 | Evans et al. |
| 7,741,618 B2 | 6/2010 | Lee et al. |
| 7,764,986 B2 | 7/2010 | Rice et al. |
| 7,777,870 B2 | 8/2010 | Hayes et al. |
| 7,788,972 B2 | 9/2010 | Terabayashi et al. |
| 7,795,014 B2 | 9/2010 | Li |
| 7,797,034 B2 | 9/2010 | Rice et al. |
| 7,797,988 B2 | 9/2010 | Schultz et al. |
| 7,800,753 B1 | 9/2010 | Hug et al. |
| 7,804,587 B2 | 9/2010 | Sanchez et al. |
| 7,822,699 B2 | 10/2010 | Katariya et al. |
| 2002/0026937 A1 | 3/2002 | Mault |
| 2002/0034757 A1 | 3/2002 | Cubicciotti |
| 2002/0034827 A1 | 3/2002 | Singh et al. |
| 2002/0058273 A1 | 5/2002 | Shipwash |
| 2002/0074553 A1 | 6/2002 | Starikov et al. |
| 2002/0109844 A1 | 8/2002 | Christel et al. |
| 2002/0110932 A1 | 8/2002 | Wagner et al. |
| 2002/0164824 A1 | 11/2002 | Xiao et al. |
| 2002/0168671 A1 | 11/2002 | Burns et al. |
| 2002/0172969 A1 | 11/2002 | Burns et al. |
| 2002/0176804 A1 | 11/2002 | Strand et al. |
| 2003/0000291 A1 | 1/2003 | Kolosov et al. |
| 2003/0052006 A1 | 3/2003 | Noca et al. |
| 2003/0052007 A1 | 3/2003 | Paul et al. |
| 2003/0100824 A1 | 5/2003 | Warren et al. |
| 2003/0138973 A1 | 7/2003 | Wagner et al. |
| 2003/0225362 A1 | 12/2003 | Currie et al. |
| 2004/0005582 A1 | 1/2004 | Shipwash |
| 2004/0005769 A1 | 1/2004 | Mikolas |
| 2004/0072356 A1 | 4/2004 | Senisterra et al. |
| 2004/0076946 A1 | 4/2004 | Trauner et al. |
| 2004/0080011 A1 | 4/2004 | Starikov et al. |
| 2004/0152076 A1 | 8/2004 | Willson et al. |
| 2004/0214177 A1 | 10/2004 | Bension |
| 2004/0253365 A1 | 12/2004 | Warren et al. |
| 2005/0014134 A1 | 1/2005 | West et al. |
| 2005/0079526 A1 | 4/2005 | Senisterra et al. |
| 2005/0084203 A1 | 4/2005 | Kane |
| 2005/0088653 A1 | 4/2005 | Coates et al. |
| 2005/0089890 A1 | 4/2005 | Cubicciotti |
| 2005/0147976 A1 | 7/2005 | Su |
| 2005/0164264 A1 | 7/2005 | Shipwash |
| 2005/0182307 A1 | 8/2005 | Currie et al. |
| 2006/0033910 A1 | 2/2006 | Sun et al. |
| 2006/0078472 A1 | 4/2006 | Momiyama et al. |
| 2006/0128917 A1 | 6/2006 | Klaerner et al. |
| 2006/0183145 A1 | 8/2006 | Turner |
| 2006/0191793 A1 | 8/2006 | Yamamoto |
| 2006/0231771 A1 | 10/2006 | Lee et al. |
| 2006/0243047 A1 | 11/2006 | Terabayashi et al. |
| 2006/0251371 A1 | 11/2006 | Schmidt et al. |
| 2007/0031861 A1 | 2/2007 | Su |
| 2007/0090026 A1 | 4/2007 | Han et al. |
| 2007/0122314 A1 | 5/2007 | Strand et al. |
| 2007/0128615 A1 | 6/2007 | Su |
| 2007/0134128 A1 | 6/2007 | Korlach |
| 2007/0154881 A1 | 7/2007 | Koo |
| 2007/0163663 A1 | 7/2007 | Strand et al. |
| 2007/0183928 A1 | 8/2007 | Neyer et al. |
| 2007/0188750 A1 | 8/2007 | Lundquist et al. |
| 2007/0206187 A1 | 9/2007 | Lundquist et al. |
| 2007/0240989 A1 | 10/2007 | Levitan et al. |
| 2007/0279626 A9 | 12/2007 | Sun et al. |
| 2007/0279631 A1 | 12/2007 | Yershov |
| 2008/0000772 A1 | 1/2008 | Bazant et al. |
| 2008/0047836 A1 | 2/2008 | Strand et al. |
| 2008/0145278 A1 | 6/2008 | Korlach |
| 2008/0157005 A1 | 7/2008 | Lundquist et al. |
| 2008/0165346 A1 | 7/2008 | Lundquist et al. |
| 2008/0255458 A1 | 10/2008 | Dunki-Jacobs et al. |
| 2008/0285039 A1 | 11/2008 | Que et al. |
| 2009/0002700 A1 | 1/2009 | Wang et al. |
| 2009/0042744 A1 | 2/2009 | Wagner et al. |
| 2009/0078036 A1 | 3/2009 | Terabayashi et al. |
| 2009/0090174 A1 | 4/2009 | Paul et al. |
| 2009/0098541 A1 | 4/2009 | Southern et al. |
| 2009/0107844 A1 | 4/2009 | Chun et al. |
| 2009/0131858 A1 | 5/2009 | Fissell et al. |
| 2009/0170118 A1 | 7/2009 | Schmidt et al. |
| 2009/0257920 A1 | 10/2009 | Facer et al. |
| 2009/0279093 A1 | 11/2009 | Van Herpen et al. |
| 2010/0032582 A1 | 2/2010 | Xia et al. |
| 2010/0075438 A1 | 3/2010 | Ho et al. |
| 2010/0097594 A1 | 4/2010 | Cho |
| 2010/0101411 A1 | 4/2010 | Tipler |
| 2010/0105035 A1 | 4/2010 | Hashsham et al. |
| 2010/0152066 A1 | 6/2010 | Malik et al. |
| 2010/0210008 A1 | 8/2010 | Strand et al. |
| 2010/0230613 A1 | 9/2010 | Pieprzyk et al. |
| 2010/0240044 A1 | 9/2010 | Kumar et al. |
| 2010/0264032 A1 | 10/2010 | Bazant |

OTHER PUBLICATIONS

A. Zukauskas, N. Kurilcik, P. Vitta, S. Jursenas, E. Bakien, R. Gaska, "Optimization of a UV light-emitting diode based fluorescence-

(56) References Cited

OTHER PUBLICATIONS phase sensor", Proc. SPIE, vol. 6398, 63980Y (2006); doi:10.1117/12.689907.

T. L. Chester and J. D. Winefordner, "Evaluation of the analytical capabilities of frequency modulated sources in multielement nondispersive flame atomic fluorescence spectrometry", Spectrochimica Acta Part B: Atomic Spectroscopy, vol. 31, Issue 1, 1976, pp. 21-29, doi:10.1016/0584-8547(76)80003-1.

Kraker, Elke, et al. "Integrated organic electronic based optochemical sensors using polarization filters." Applied Physics Letters 92.3 (2008): 033302-033302.

Pais, Andrea, et al. "High-sensitivity, disposable lab-on-a-chip with thin-film organic electronics for fluorescence detection." Lab on a Chip 8.5 (2008): 794-800.

Schreiber, Ulrich, et al. "Measurement of chlorophyll fluorescence within leaves using a modified PAM fluorometer with a fiber-optic microprobe." Photosynthesis research 47.1 (1996): 103-109.

Webster, J. R., et al. "Monolithic capillary electrophoresis device with integrated fluorescence detector." Analytical chemistry 73.7 (2001): 1622-1626.

Schreiber, U., et al. "Assessment of photosynthetic performance of Prochloron in Lissoclinum patella in hospite by chlorophyll fluorescence measurements." Plant and Cell Physiology 38.8 (1997): 945-951.

Jorgensen, Anders M., et al. "A biochemical microdevice with an integrated chemiluminescence detector." Sensors and Actuators B: Chemical 90.1 (2003): 15-21.

Khandurina, Julia, and András Guttman. "Bioanalysis in microfluidic devices." Journal of Chromatography A 943.2 (2002): 159-183.

Roháček, Karel, and Miloš Barták. "Technique of the modulated chlorophyll fluorescence: basic concepts, useful parameters, and some applications." Photosynthetica 37.3 (1999): 339-363.

Nedbal, Ladislav, et al. "Kinetic imaging of chlorophyll fluorescence using modulated light." Photosynthesis Research 66.1-2 (2000): 3-12.

Kim, Young-Hwan, et al. "Poly (dimethylsiloxane)-based packaging technique for microchip fluorescence detection system applications." Microelectromechanical Systems, Journal of 15.5 (2006): 1152-1158.

Rolfe, Stephen A., and Julie D. Scholes. "Quantitative imaging of chlorophyll fluorescence." New Phytologist 131.1 (1995): 69-79.

Kurilčik, Natalija, et al. "Fluorescence detection of biological objects with ultraviolet and visible light-emitting diodes." Optica Applicata 36.2-3 (2006).

Chester, Thomas Lee. Analytical potential of a selectively modulated interferometric dispersive spectrometer. Diss. University of Florida, 1976.

P. Herman, et al., "Frequency Domain Fluorescence Microscopy with the LED as a Light Source", J. Microscopy 203, part 2, Aug. 2001, pp. 176-181.

Haase, Anja, and Elke Kraker. "Sensing & Measurement Separating excitation light from luminescence", SPIE 2008 (10.1117/2.1200805.1139).

Cai, Yuankun. "Organic light emitting diodes (OLEDs) and OLED-based structurally integrated optical sensors." (2010). Ph.D. Dissertation Iowa State University.

Erickson, David, et al. "Nanofluidic tuning of photonic crystal circuits." Integrated Optoelectronic Devices 2007. International Society for Optics and Photonics, 2007.

Monat, C., P. Domachuk, and B. J. Eggleton. "Integrated optofluidics: A new river of light." Nature photonics 1.2 (2007): 106-114.

Ros, Alexandra, et al. "Towards single molecule analysis in PDMS microdevices: from the detection of ultra low dye concentrations to single DNA molecule studies." Journal of biotechnology 112.1 (2004): 65-72.

Shin, Kyeong-Sik, et al. "Characterization of an integrated fluorescence-detection hybrid device with photodiode and organic light-emitting diode." Electron Device Letters, IEEE 27.9 (2006): 746-748.

Shen, L., et al. "Use of a low-cost CMOS detector and cross-polarization signal isolation for oxygen sensing." Sensors Journal, IEEE 11.6 (2011): 1359-1360.

Shen, Li, et al. "A CMOS optical detection system for point-of-use luminescent oxygen sensing." Sensors and actuators B: Chemical 155.1 (2011): 430-435.

\* cited by examiner

SIMULTANEOUS, SINGLE-DETECTOR FLUORESCENCE DETECTION OF MULTIPLE ANALYTES WITH FREQUENCY-SPECIFIC LOCK-IN DETECTION

CROSS REFERENCE TO RELATED APPLICATIONS

The present application claims benefit of priority from U.S. Provisional Patent Application No. 61/407,887, Oct. 28, 2010, the entirety of which is expressly incorporated herein by reference.

STATEMENT OF GOVERNMENT RIGHTS

This invention was made with government support under award number ECCS-0930305 awarded by the National Science Foundation. The Government has certain rights in the invention.

BACKGROUND OF THE INVENTION

Microfluidics and lab-on-a-chip hold the promise of miniaturized biological and chemical testing [1], and many microfluidic systems have been demonstrated for the purposes of electrophoresis [1], genetic analysis [2], and chemiluminescence assays [3]. One additional technique that is commonly used in such systems is fluorescence. When illuminated with light of a particular color (the excitation wavelength), fluorescent materials luminesce in a different color (the emission color). The intensity of the emitted light relates to the concentration of the fluorescent dye. This is the most commonly used approach in the mainstream biological analyses.

Fluorescence detection systems, however, have proven difficult to miniaturize [4], though many different systems have been proposed [5,6]. See also, U.S. Pat. Nos. 7,800,753; 7,525,653; 7,795,014; 7,709,249; 7,659,968; 7,653,429; 7,569,382; 7,563,350; 7,550,069; 7,531,363; 7,515,953; 7,511,811; 6,995,841; 7,507,575; 7,463,353; 7,444,053; 7,142,303 6,686,201; 6,038,023; and 5,784,157, and US Published Patent Application Nos. 2002/0109844, 2010/0032582, each of which is expressly incorporated herein by reference. Fluorescence measurements typically require optical sources, lenses and detectors, and these components are difficult to miniaturize and integrate effectively on a lab-on-a-chip. Typically, optical filters are used to shield the detector or sensor, and these optical filters have to be specifically matched to the excitation light and the dye. For example, the Rhodamine 6G-specific filter used in a fluorescence microscope shields excitation (green) light but passes emission (red) light through to the eyepiece.

Shown in FIG. 1 is a polarization-based optical isolation technique which has recently been demonstrated [7,8]. It has the advantage of being color-independent, and as such does not require different filters for different colors. Here, the excitation light is polarized before being incident on the dye, and a cross-polarized filter after the dye blocks most of the excitation light from the filter. The emission light, which is un-polarized, is then detected.

In its simplest implementation, it can only quantify a single dye at a time, since the sensor cannot discriminate the color of the incident light.

The application of fluorescence detection techniques in conjunction with microelectromechanical systems (MEMS) including types of lab-on-a-chip is known. See, e.g., U.S. Pat. Nos. 7,800,753; 7,797,988; 7,788,972; 7,741,618; 7,723,116; 7,722,753; 7,715,001; 7,708,873; 7,692,783; 7,691,244; 7,645,596; 7,630,073; 7,612,883; 7,598,371; 7,590,161; 7,586,604; 7,531,363; 7,525,653; 7,476,504; 7,465,382; 7,463,353; 7,461,547; 7,444,053; 7,302,830; 7,291,564; 7,259,217; 7,215,425; 7,163,658; 7,087,444; 7,016,022; 6,986,739; 6,934,836; 6,934,435; 6,887,202; 6,881,979; 6,846,638; 6,762,025; 6,716,948; 6,685,810; 6,682,942; 6,608,360; 6,596,545; 6,379,929; 6,331,439; 6,287,765; 6,118,126; 5,980,704; 5,603,351, and US Published Patent Application Nos. 2010/0264032; 20100240044; 2010/0230613; 2010/0210008; 2010/0152066; 2010/0105035; 2010/0101411; 2010/0097594; 2010/0075438; 2009/0279093; 2009/0257920; 2009/0170118; 2009/0131858; 2009/0107844; 2009/0098541; 2009/0090174; 2009/0078036; 2009/0042744; 2009/0002700; 2008/0285039; 2008/0255458; 2008/0165346; 2008/0157005; 2008/0145278; 2008/0047836; 2008/0000772; 2007/0279631; 2007/0279626; 2007/0240989; 2007/0206187; 2007/0188750; 2007/0183928; 2007/0163663; 2007/0154881; 2007/0134128; 2007/0128615; 2007/0122314; 2007/0090026; 2007/0031861; 2006/0251371; 2006/0243047; 2006/0231771; 2006/0191793; 2006/0183145; 2006/0128917; 2006/0078472; 2006/0033910; 2005/0182307; 2005/0164264; 2005/0147976; 2005/0089890; 2005/0088653; 2005/0084203; 2005/0079526; 2005/0014134; 2004/0253365; 2004/0214177; 2004/0152076; 2004/0080011; 2004/0076946; 2004/0072356; 2004/0005769; 2004/0005582; 2003/0225362; 2003/0138973; 2003/0100824; 2003/0052007; 2003/0052006; 2003/0000291; 2002/0176804; 2002/0172969; 2002/0168671; 2002/0164824; 2002/0110932; 2002/0074553; 2002/0058273; 2002/0034827; 2002/0034757; 2002/0026937, each of which is expressly incorporated herein by reference.

See also, K. G. Libbrecht, E. D. Black, and C. M. Hirata, "A basic lock-in amplifier experiment for the undergraduate laboratory" Am. J. Phys. 71, pp. 1208. authors.library-.caltech.edu/12641/1/LIBajp03.pdf; Joseph R. Lakowicz, *Principles of fluorescence spectroscopy*, Springer, 2006, p. 743; P. Herman, et al., "Frequency Domain Fluorescence Microscopy with the LED as a Light Source", J. Microscopy 203, part 2, August 2001, pp. 176-181; A. Zukauskas, N. Kurilcik, P. Vitta, S. Jursenas, E. Bakien, R. Gaska, "Optimization of a UV light-emitting diode based fluorescence-phase sensor", Proc. SPIE, Vol. 6398, 63980Y (2006); doi:10.1117/12.689907; T. L. Chester and J. D. Winefordner, "Evaluation of the analytical capabilities of frequency modulated sources in multielement non-dispersive flame atomic fluorescence spectrometry", Spectrochimica Acta Part B: Atomic Spectroscopy, Volume 31, Issue 1, 1976, Pages 21-29, doi: 10.1016/0584-8547(76)80003-1; U. Schreiber, "Detection of rapid induction kinetics with a new type of high-frequency modulated chlorophyll fluorometer", Photosynthesis Research, Volume 9, Numbers 1-2, 261-272, DOI: 10.1007/BF00029749.

SUMMARY OF THE INVENTION

In order to provide capability of detection of multiple simultaneous fluorophores, the optical source can be modulated, with synchronous detection of the emission. More particularly, concurrent optical excitation for different excitation wavelengths can be modulated at different frequencies, with the sensor signal analyzed to distinguish between signal components corresponding to the various excitation signals. Further, crossed polarizers, or other excitation signal blocking technology may be employed to isolate the excitation signal from the received signal. Thus, the sensor may be a broad band, high sensitivity detector, preferably with a high dynamic range, which is useful for the accurate analysis of simultaneous emissions.

According to one aspect of the technology, monochromatic excitations, such as laser excitation or optically filtered excitation, is linearly polarized and projected onto a sample containing fluorescent dyes or materials. The fluorescent dyes or materials emit wavelength shifted emissions, typically with a longer wavelength than the excitation. The emission, especially from a soluble dye or solution, is unpolarized, and therefore a significant fraction will pass through the second polarizer cross with respect to the first, providing a high signal to noise ratio between the excitation source(s) and the respective fluorescence emission(s).

Stokes shift is the difference (in wavelength or frequency units) between positions of the band maxima of the absorption and emission spectra of the same electronic transition. When a system absorbs a photon, it gains energy and enters an excited state. One way for the system to relax is to emit a photon, thus losing its energy. The difference between the energy of the emitted and excitation energy is the Stokes shift, with a reduction in energy being represented as a positive shift. If the emitted photon has more energy, the energy difference is called an anti-Stokes shift. Compared to conventional color filtering, polarization filtering allows for an extremely minimal Stokes shift between the emission and excitation wavelength of a particular dye, not limited by the transfer function of a color filter. This is a functional advantage of polarization filtering over color filtering.

An AC drive may be incorporated into the optical source(s). A system with multiple light sources driven at multiple frequencies using lock-in detection locked separately to each frequency allows the sensor to distinguish between different dyes. More generally, the technique employs a plurality of temporally modulated excitation beams, which each contribute to a set of superposed signals within a common sensor output, which are then coherently detected based on the various temporal modulation patterns. The excitation beams are polarized, so that the polarized source illumination may be distinguished from the scattered secondary emission by a polarizing detector. By combining polarization filtering and AC coherent detection, the system with a single sensor and optical filters may simultaneously quantify more than one dye.

As an alternate to simple frequency modulation, it is also possible to use a direct sequence or frequency hopping spread spectrum excitation. For example, over long integration times, spread spectrum may avoid permit a greater number of excitation sources to coexist, while maintaining signal isolation. Further, an adaptive excitation scheme may be employed, for example to alter an excitation pattern where interference is evident, or where higher sensitivity for an analyze is desired. For example, if a high strength signal corresponding to a particular fluorophore is seen in the output, the excitation pattern for the corresponding light source may be modified to have reduced power, to optimize the linearity of detection and/or mutual interference. Likewise, if a signal is very weak, the corresponding excitation may be increased in power. If there appears to be interference, different excitation sources may be driven at mutually exclusive times. Thus, the excitation pattern may be modified in dependence on the sensor output. Of course, a set of frequency modulated emitters can also be adaptively driven, and especially may be respectively modulated in amplitude.

The present technique was tested to simultaneously quantify two different dyes using a common sensor. A system to drive and measure multiple dyes was built and tested, and detection limits down to 10 nM were demonstrated. Such a system is readily adapted to and configured for lab-on-a-chip microfluidic systems, in which parallel fast quantification without optical filters is desirable.

Advantageously, the optical emitters are light emitting diodes, and more preferably, organic light emitting diodes. The later may be selectively patterned on a polymer substrate, for example on a polarizer sheet or material, which is provided near or on the surface of a mechanical system, such as a micromachined liquid processing system, which may be a lab-on-a-chip. While intrinsic polarization of crystalline polymers may be employed to seek isolation of optical signals, it is preferred that high quality polarizers be employed to achieve high signal to noise ratios, such as J-sheet (aligned herapathite) or H-sheet (aligned polyvinyl alcohol treated with iodine), though these may be formed on an intrinsic surface rather than a separate film.

Light from the various sources, which are preferably selected to have sufficient monochromaticity (at least within a band of interest) to provide a high specific emission from the fluorophore while avoiding crosstalk between the different dyes of interest (and other possible sources of fluorescence).

It is therefore an object of the invention to provide a system and method for concurrently analyzing a liquid or amorphous material sample for a presence of a plurality of different scattered optical emissions, each optimally excited by a different optical wavelength of light, comprising providing a plurality of controllable optical sources, each having different optical wavelength characteristics; controlling the plurality of controllable optical sources to each have a concurrent but different temporal excitation pattern; illuminating a sample with light from the plurality of controllable optical sources through a polarizer; collecting light from the sample, comprising polarized light from the plurality of controllable optical sources, and scattered light from the liquid or amorphous material in the sample; and passing it through a second polarizer which substantially blocks the polarized light from the plurality of controllable optical sources, while passing a substantial portion of scattered light from the liquid or amorphous material in the sample; and detecting the scattered light from the liquid or amorphous material in the sample passing through the second polarizer, with an optical sensor having sufficient linearity to allow algorithmic separation and quantification of the respective concurrent plurality of different scattered optical emissions based on their respective different temporal excitation patterns.

According to a preferred embodiment, the scattered light comprises fluorescent emissions from different fluorophores, such as fluorescent dyes which tag analytes in a liquid sample.

According to one embodiment, the respective different temporal excitation patterns comprise different frequencies of modulation. According to another embodiment, the respective different temporal excitation patterns comprise distinct spread spectrum excitation patterns. According to a still further embodiment, the amplitude and/or temporal pattern of excitation is adaptive to a signal represented in the output of the sensor. According to another embodiment, a sensor is provided to measure an optical emission from one or more of the plurality of controllable optical sources. Preferably, each of the controllable optical sources has a separate intensity measurement, which may be before or after the first polarizer. Preferably, the scattered light corresponding to a respective controllable optical source has an intensity which is proportional to an intensity of the light and a concentration or amount of an analyte in the optical path, and the measured intensity measurement is used to control for the intensity of the respective controllable optical source.

According to one embodiment, the optical path between the plurality of controllable optical sources and the sensor is line of sight. According to another embodiment, the fluorescence is measured off-axis to the plurality of controllable optical sources. Indeed, in the case of off-axis detection, the polarizers may be dispensed with.

According to a further embodiment, a non-specific scattering from the sample is controlled by an illumination which does not excite a specific scattering. Alternately, a control scattering dye or material is placed in the sample having a known scattering emission, and a deviation from the known emission is used to calibrate the output using a background subtraction algorithm.

According to a still further embodiment, a plurality of sensors and/or detectors are provided to concurrently measure emissions representing the plurality of analytes, each having concurrent signal components in a plurality of the sensors and/or detectors.

The present invention provides, according to one embodiment, a fluorescent detection system having direct illumination configuration, suitable for use with microfluidics, that is color independent and can be used to simultaneously or concurrently quantify multiple fluorophores. The system need not be custom designed for particular dyes, so long as the excitation illumination sources have distinct spectral characteristics which interact differently with the various analytes, and the sensor or sensors are able to accurately quantify the simultaneous optical emissions. Thus, the system is not limited from use to quantify analytes having complex spectral signatures, using a mathematical technique, such as principal component analysis (PCA), to quantitatively distinguish between the various components. Indeed, since there will generally be some contribution to the net optical emission from each analyte under each illumination condition, a variety of statistical techniques may be employed to optimally predict the concentration of each component.

Therefore, according to preferred embodiment of the present technology, the system provides a simple optical path, e.g., line of sight from each of a plurality of illumination sources, through a sample sandwiched between a pair of crossed polarizers, to an optical sensor, seeking to selectively determine an amount of optical emission from only a single analyte corresponding to excitation by a single illumination source, with a plurality of different illumination sources available to quantify a plurality of simultaneous analytes. The optical path may be more complex, for example employing total internal reflection optics to receive light from the various sources and guide it to the sample. Generally, the optical path is not reflected, though reflective optics may be employed as appropriate given the polarized beam detection system.

According to an alternate embodiment, any requirement that a single analyte by excited only by a single light source is relaxed, and an orthogonal decomposition analysis of the results of varying spectral composition illumination is performed to determine the sample composition.

Principal component analysis (PCA) involves a mathematical procedure that transforms a number of possibly correlated variables into a smaller number of uncorrelated variables called principal components. The first principal component accounts for as much of the variability in the data as possible, and each succeeding component accounts for as much of the remaining variability as possible. Depending on the field of application, it is also named the discrete Karhunen-Loève transform (KLT), the Hotelling transform or proper orthogonal decomposition (POD). See, en.wikipedia.org/wiki/Principal_component_analysis, expressly incorporated herein by reference. PCA is mathematically defined as an orthogonal linear transformation that transforms the data to a new coordinate system such that the greatest variance by any projection of the data comes to lie on the first coordinate (called the first principal component), the second greatest variance on the second coordinate, and so on. PCA is theoretically the optimum transform for given data in least square terms. For a data matrix, $X^T$, with zero empirical mean (the empirical mean of the distribution has been subtracted from the data set), where each row represents a different repetition of the experiment, and each column gives the results from a particular probe, the PCA transformation is given by: $Y^T = X^T W = V\Sigma^T$, where the matrix $\Sigma$ is an m-by-n diagonal matrix with nonnegative real numbers on the diagonal and $W\Sigma V^T$ is the singular value decomposition (svd) of X. See, en.wikipedia.org/wiki/Singular_value_decomposition, expressly incorporated herein by reference.

Given a set of points in Euclidean space, the first principal component (the eigenvector with the largest eigenvalue) corresponds to a line that passes through the mean and minimizes sum squared error with those points. The second principal component corresponds to the same concept after all correlation with the first principal component has been subtracted out from the points. Each eigenvalue indicates the portion of the variance that is correlated with each eigenvector. Thus, the sum of all the eigenvalues is equal to the sum squared distance of the points with their mean divided by the number of dimensions. PCA essentially rotates the set of points around their mean in order to align with the first few principal components. This moves as much of the variance as possible (using a linear transformation) into the first few dimensions. The values in the remaining dimensions, therefore, tend to be highly correlated and may be dropped with minimal loss of information. PCA is often used in this manner for dimensionality reduction. PCA has the distinction of being the optimal linear transformation for keeping the subspace that has largest variance. This advantage, however, comes at the price of greater computational requirement if compared, for example, to the discrete cosine transform. Nonlinear dimensionality reduction techniques tend to be more computationally demanding than PCA. However, because of interaction of dyes, multiple photon absorption and other quantum effects, quenching, fluorescent resonant electron transfer, etc., a nonlinear technique, such as kernel PCA, may prove useful. Likewise, a linear discriminant analysis technique may also be employed. The PCA may, for example, be computed using an expectation minimization technique.

An autoencoder neural network with a linear hidden layer is similar to PCA. Upon convergence, the weight vectors of the K neurons in the hidden layer will form a basis for the space spanned by the first K principal components. Unlike PCA, this technique will not necessarily produce orthogonal vectors. However, according to one embodiment, the analyzer comprises a neural network trained to produce outputs which represent the quantity of various analytes, e.g., fluorescent dyes or tags, in a sample.

See, Jolliffe I. T. "Principal Component Analysis", Series: Springer Series in Statistics, 2nd ed., Springer, NY, 2002, XXIX, 487 p. 28 illus. ISBN 978-0-387-95442-4; A. A. Miranda, Y. A. Le Borgne, and G. Bontempi. "New Routes from Minimal Approximation Error to Principal Components", Volume 27, Number 3/June, 2008, Neural Processing Letters, Springer; Jonathon Shlens, "A Tutorial on Principal Component Analysis." Citeseer 10.1.1.115.3503; Roweis, Sam. "EM Algorithms for PCA and SPCA." Advances in Neural Information Processing Systems. Ed. Michael I. Jordan, Michael J. Kearns, and Sara A. Solla The MIT Press, 1998, each of which is expressly incorporated herein by reference.

Thus, the analysis of the signal may be more complex than simply demodulating an encoded signal using a bank of frequency selective filters, and the present techniques permit such complex analysis.

According to one embodiment, the illumination may be provided by a tunable liquid crystal optical filter or other spectrally tunable optic, which is dynamically controlled to provide at least two different spectral outputs. See, U.S. Pat. Nos. 6,403,947, 7,797,034, 7,804,587, 7,777,870, 7,764,986, 7,603,167, 7,555,332, 7,474,399, 7,474,398, 7,466,418, 7,417,796, 7,403,812, 7,372,567, 7,362,489, 7,336,323, RE39,977, 7,239,388, 6,965,431, 6,870,612, 6,858,852, 6,545,739, 6,075,5, 5,863,504, 5,835,214, 5,817,462, 5,784,162, www.olympusmicro.com/primer/java/filters/lctf/index.html, www.meadowlarkoptics.com/products/lcFiltersLanding.php, www.sci-sol.com/lcproperties.pdf, each of which is expressly incorporated herein by reference. The present technology generally avoids need for a spectrometer associated with the sensor.

While the illumination for the detection system may come from a variety of sources, and indeed the different illumination conditions need not all derive from the same type of emitter, a preferred system provides a organic light emitting diode material formed in close proximity to the sensor space, and for example may be formed on a polarizer sheet or laminated to the polarizer sheet. In accordance with one aspect of the technology, a plurality of different organic light emitting diode structures, with respectively different spectral characteristics, play be placed in close proximity to the sensor space, and be exited with respectively different temporal patterns of illumination. Another embodiment provides a stack of different light emitting elements with transparent electrode materials. A still further embodiment provides fiber optics or refractive optics or total internal reflection optics to bring the illumination from different sources to a common sensor space.

It is therefore an object to provide a system configured for concurrently analyzing a sample for a presence of a plurality of analyzes, comprising: a plurality of controllable optical sources, each configured to concurrently emit light having different optical wavelength characteristics; a control, configured to cause the plurality of controllable optical sources to each have a concurrent but different temporal optical emission pattern; a first polarizer having a first polarization axis, disposed within an optic path of the plurality of controllable optical sources; a sample space illuminated by polarized light from the first polarizer; a second polarizer, having a second polarization axis orthogonal with respect to the first polarization axis, receiving light from the sample space, and selectively substantially passing scattered light from the sample space and selectively substantially blocking light from the first polarizer having the first polarization axis; a sensor, detecting the scattered light passing through the second polarizer; and a lock-in detector, receiving an output from the sensor, configured to determine a concentration of at least one analytes in the sample based on a temporal analysis of the sensed scattered light in dependence on the concurrent but different temporal optical emission pattern of the plurality of controllable optical sources.

It is also an object to provide a method for concurrently measuring concentrations of a plurality of analytes in a sample, each displaying a different illumination-wavelength sensitive scattering, comprising: illuminating a sample space with polarized illumination from a plurality of controllable optical sources, each configured to concurrently emit light having different optical wavelength characteristics and a concurrent but different temporal optical emission pattern; passing scattered light and polarized illumination from the sample space through a polarizer which blocks the polarized illumination and substantially passes the scattered illumination; and receiving and analyzing the scattered light with a lock-in detector, to determine a concentration of the analyte in the sample based on a temporal analysis of the received scattered light, in dependence on the concurrent but different temporal optical emission pattern of the plurality of controllable optical sources.

It is a further object to provide a method for analyzing a sample for an analyte having an illumination-wavelength sensitive scattering, comprising: illuminating a sample space with a plurality of different spectral characteristic, differently temporally modulated, polarized emission patterns; detecting scattered light from the sample space while blocking polarized light from the polarized emission patterns; and analyzing the detected scattered light with respect to the respective temporal modulation of the plurality of emission patterns, to distinguish between emissions associated with each of the different spectral characteristics; and outputting a signal in dependence on the analyzing.

It is a still further object to provide an analyzer for detecting an illumination-wavelength sensitive scattering, comprising: an illuminator subsystem configured to illuminate a sample space with a plurality of different spectral characteristic, differently temporally modulated, polarized emission patterns; a sensor configured to selectively detect scattered light from the sample space while blocking an effect of polarized light from the polarized emission patterns; and a processor configured to analyze an output of the sensor with respect to the temporal modulation patterns, and producing an output selectively dependent on emissions associated with at least one of the spectral characteristics.

The analyte may comprise a plurality of different analytes, each optimally excited by a different optical wavelength of light, and producing a scattered optical emission selectively dependent on the intensity of illumination at an optimal wavelength of light. The sample may comprise a liquid or amorphous material. The sample may comprise a fluorescent dye. The sample may comprise a plurality fluorescent dyes each having different optical absorption characteristics. The at least two of the plurality of dyes may have overlapping spectral emission characteristics.

The sensor or lock-in detector preferably has sufficient linearity to allow algorithmic separation and quantification of a respective concurrent plurality of different scattered optical emissions based on their respective different temporal excitation patterns.

The respective different temporal excitation patterns may comprise different frequencies of modulation. The respective different temporal excitation patterns may also comprise different spread spectrum modulation patterns of optical intensity. The spread spectrum modulation patterns may comprise a direct sequence spread spectrum pattern. The lock-in detector may further determine an optical scattering of a sample which is independent of an analyte concentration.

The amplitude of optical emission of at least one controllable optical source may be adaptive to the output of the sensor. A temporal pattern of optical emission of at least one controllable optical source may be adaptive to the output of the sensor. The method may further comprise adapting an amplitude of optical emission of at least one controllable optical source to an output of the detector.

The system may further comprise at least one transducer configured to measure an optical emission magnitude of at least one of the plurality of optical sources. The system may further comprise at least one transducer configured to separately measure an optical emission magnitude of each of the plurality of optical sources.

These and other object will become apparent from a review of the drawings and detailed description of the preferred embodiments.

DETAILED DESCRIPTION OF THE PREFERRED EMBODIMENTS

Experimental Setup

A. Dyes

Figure 1:
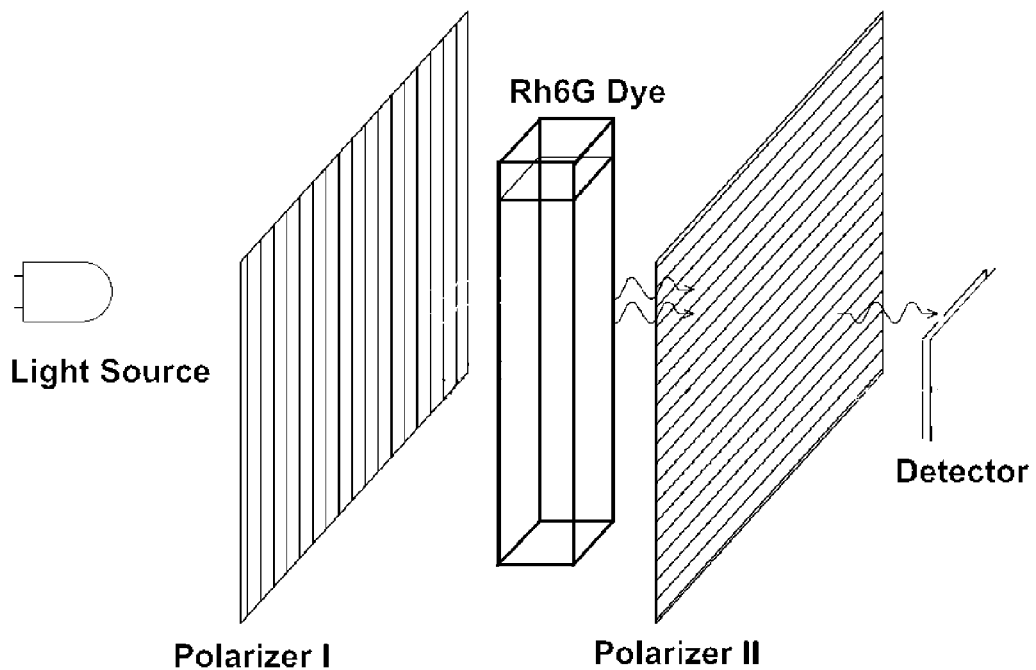
FIG. 1 shows a basic schematic diagram of polarization filtering according to the prior art.
Figure 2:
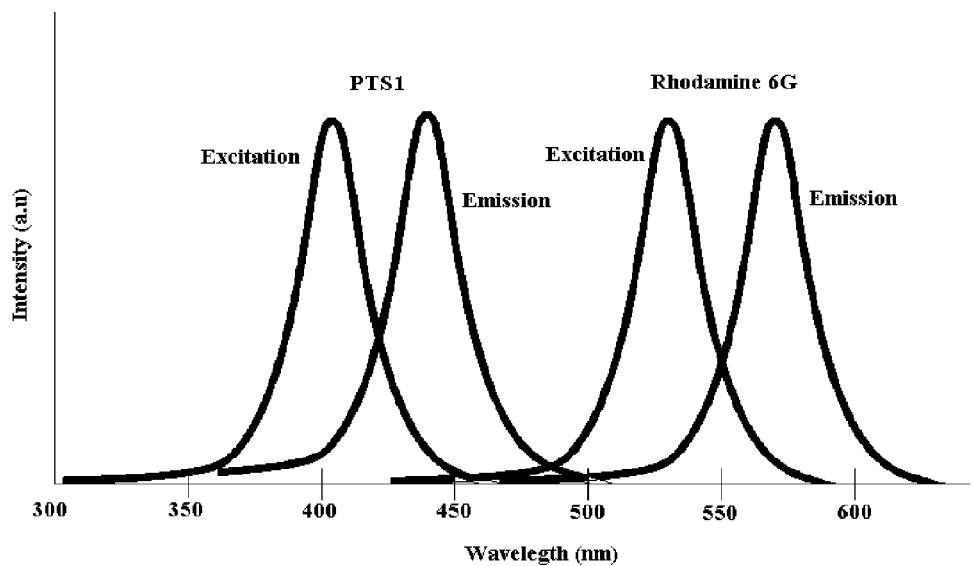
FIG. 2 shows a schematic illustration of the absorption and emission spectra of Rh6G and PTS1.

For proof-of concept, two different fluorescent dyes having different excitation wavelengths, as shown in FIG. 2, were selected. To use this method, it is necessary for the two dyes to have distinct excitation wavelengths. As will be discussed, it is the frequency of the response, and not the color, that a locked-in photodetector detects; the two dyes could overlap in emission wavelength and still be distinguished by lock-in detection.

The dyes selected are Rhodamine 6G (Rh6G), which has an absorption maximum at 530 nm and a peak emission wavelength of 566 nm; and trisodium 8-methoxypyrene-1,3, 6-trisulfonate (PTS1) which has its absorption maximum at 404 nm and a peak emission wavelength of 430 nm. Both the emission and excitation wavelengths of the two dyes are distinct.

Figure 3:
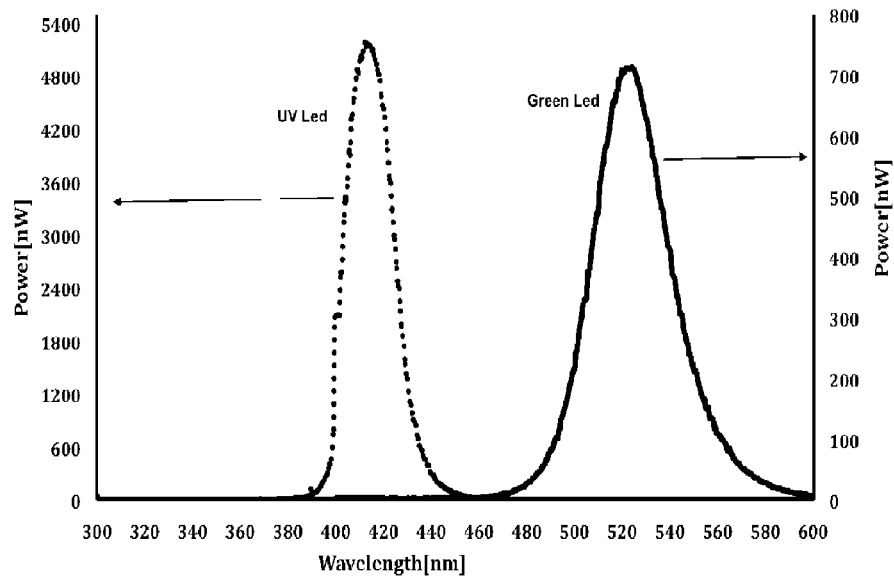
FIG. 3 shows the spectral output of LED light sources

FIG. 3 shows the emission spectra of the two LEDS used as excitation sources. As can been seen, the green LED has an emission peak of 525 nm and extends about 100 nm, and the blue/UV has an emission peak of 400 nm and extends about 50 nm. There is no significant overlap in emission spectra.

To make precise concentrations of the two dyes, precise amounts of dye powder were weighed on a microbalance and mixed with specific volumes of distilled water. 1 mM standard solutions were made with both dyes, and then further diluted as standards to make more dilute solutions. Every solution is stirred thoroughly to ensure uniform concentrations. Concentrations from $10^{-3}$ to $10^{-9}$M were mixed to create a full experimental matrix of mixtures of both dyes at all ranges of concentration in a factor-of-ten dilution series.

B. Physical Setup

Figure 4:
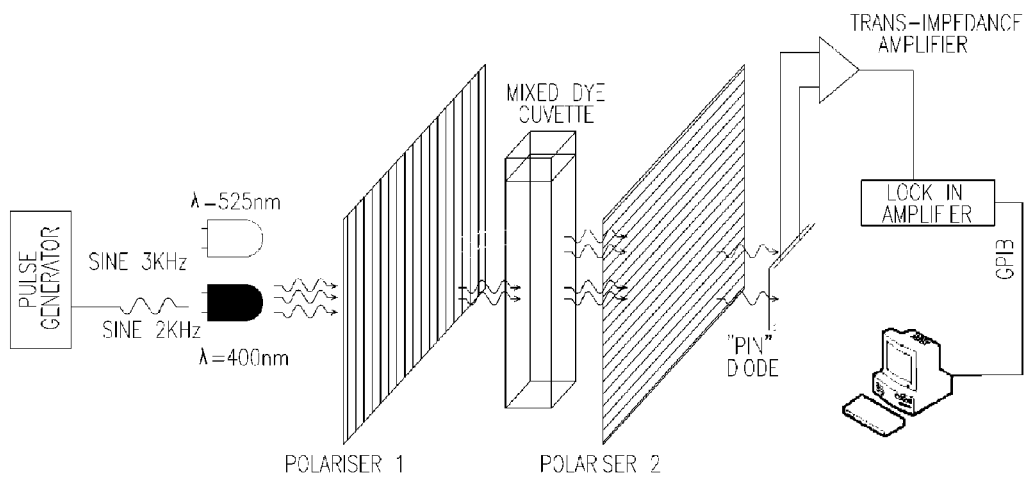
FIG. 4 shows a schematic of the lock-in detection setup according to an embodiment of the present invention.

The schematic diagram of the setup is shown in FIG. 4. Two LEDs are driven separately with different frequencies, and two polarizing films (Edmund Optics NT45-667) oriented at 90 degrees are used to isolate the excitation light from the emission light. A 3 mL cuvette holder between them contained the dye sample. In this experiment, the cuvette is a standard square cuvette with an optical path length of 10 mm and capacity of 3.5 mL.

C. Modulation Frequency

Figure 5:
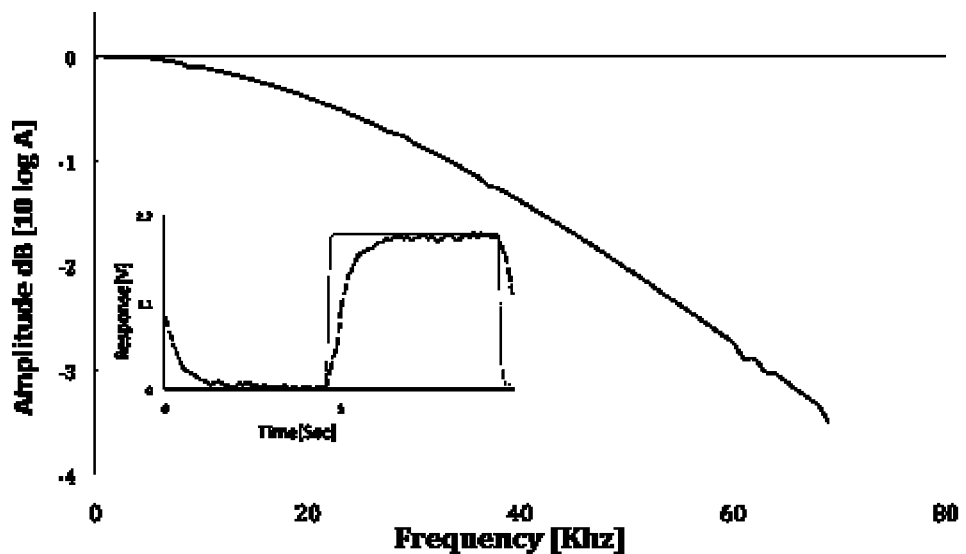
FIG. 5 shows frequency and time domain response of the system according to FIG. 4.

Before determining the modulation frequencies of the separate diodes, the modulation frequency of the system was evaluated to ensure that the diode response is not limited by the PIN diode or other electronics. An LED was driven directly by a signal generator by a sine wave from 0 to ~2 V at frequencies from 1 KHz to 100 KHz and the AC response at the output of the transimpedance amplifier measured by an AC voltmeter. The 3 dB bandwidth of system is shown in FIG. 5. The bandwidth of the system was 63 KHz Another way of evaluating system speed is in the time response to a square wave input. The LED was pulsed with a square voltage, and the output out of the transimpedance amplifier was measured on the scope. This system time response is shown in FIG. 5, which has rise time (signal rise time 10% to 90% of its maximum value) of 5 ms or ~20 KHz.

The modulation frequencies for the LEDs were chosen to be 2 and 3 KHz, well below either cutoff. The input voltage ranges on the LED are picked so as to not saturate the detector when both LEDS are on and give clean signals for both 2 kHz and 3 kHz signal.

The crossed polarizers reduce the magnitude of the detector photocurrent due to excitation light by about 25 dB. The signal output from detector goes through transimpedance amplifier to translate the nanoAmperes of photocurrent into tenths of volts of response.

D. Base-Line Response to DC Excitation

Figure 6:
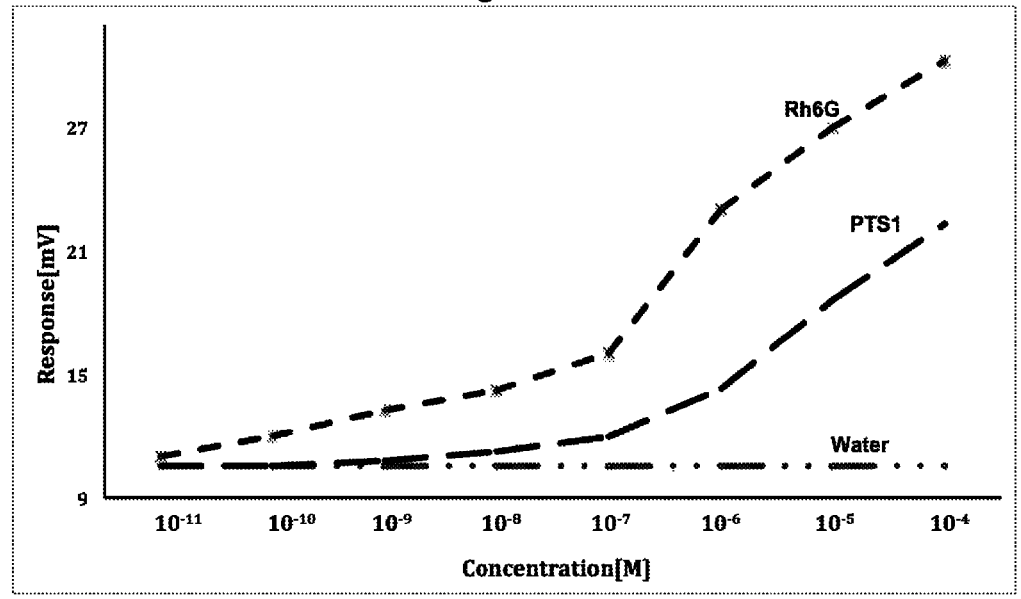
FIG. 6 shows the DC response for PTS1 and Rh6G dyes.

Dye samples for both Rh6G by itself, and PTS1 by itself are made with concentrations from 0.1 mM to 0.01 nM. The DC photovoltage response directly out of the photodetector is measured and plotted in FIG. 6. The horizontal line in both figures demonstrates the response for a 0 M concentration of distilled water. This gives a background signal floor to the fluorescence measurements.

The minimum concentration that can be read, the limit of detection, is determined by the amount of noise in the signal compared to the amplitude of the signal. The noise level of the signal is estimated by taking the variation of the time-series measurements of the background water. At the lowest concentration measured of 10 nm for PTS1 and 100 pM for Rh6G, the signal was 10 mV higher than the background, with a signal-to-noise ratio of ~3.

The DC response demonstrated detectability down to about the 10 nM range. However, measurement of DC photocurrent means the system is susceptible to ambient background light variations. In addition, without wavelength-specific optical filters, the system cannot distinguish between different colors of emission. Both of these disadvantages are overcome by using lock-in detection.

E. Lock-In Detection

With lock-in detection, the LEDS are driven at a specific frequency, and the photodetector is connected to a transimpedance amplifier. The output of the transimpedance amplifier is connected to a Princeton Electronics Digital Lock-in Amplifier, locked to the source frequency. The response measured by the lock-in is the response only at the frequency of the driven LED, and noise at other frequencies is not detected. Such lock-in detectors have excellent ability to discriminate between signal and noise, and can detect nanoVolts of signal in the presence of noise many orders of magnitude larger.

Use of the lock-in eliminated DC ambient noise, and allowed emission light from different dyes to be distinguished by modulation frequency. The emission light at 2 kHz reflected the concentration of dye excited by a 2 kHz source, largely regardless of the background amount of dye driven by a 3 kHz LED. This technique also eliminated cross-fluorescence (in which luminescence form one dye acted as an excitation for another); the cross-fluorescence signal will be at a different frequency, and so ignored by the lock-in.

F. Experimental Measurements for Lock-In Detection

Figure 7A:
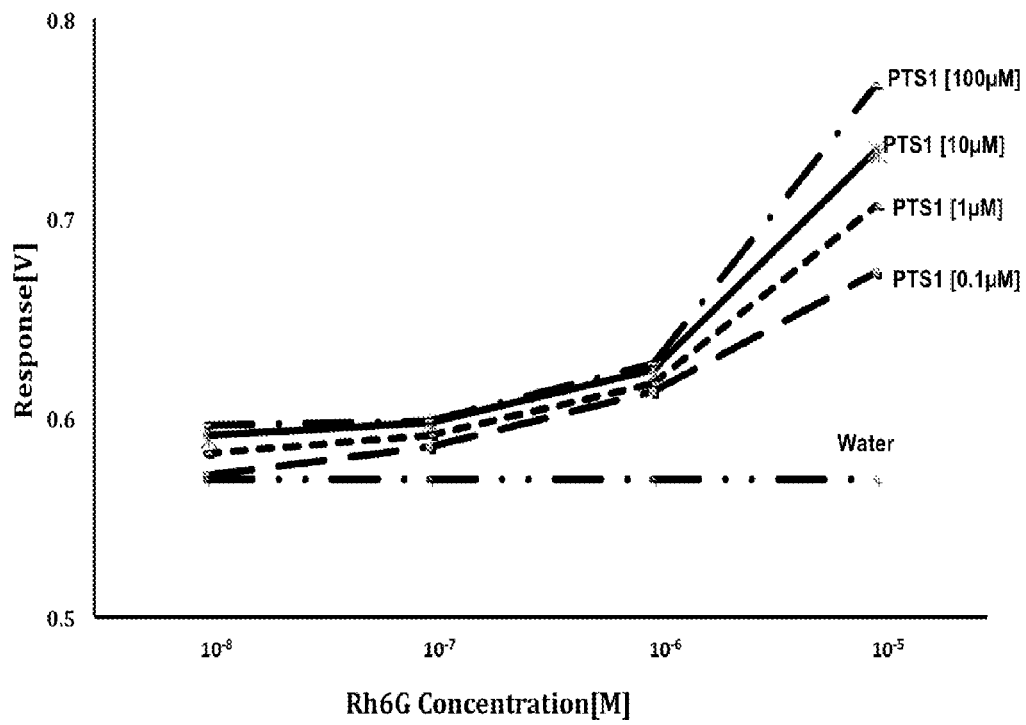
FIG. 7A shows the response of the system of FIG. 4 with respect to concentration of Rh6G measured with lock-in detection.
Figure 7B:
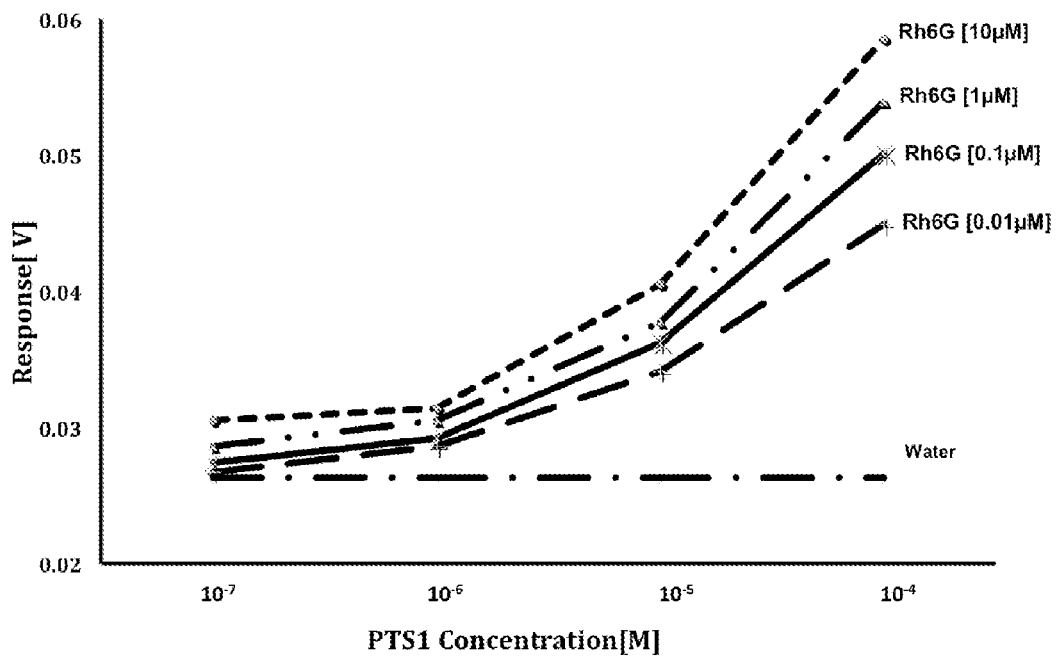
FIG. 7B shows the response of the system of FIG. 4 with respect to concentration of PTS1 measured with lock-in detection. Each line represents a curve with a specific background concentration of the other dye.

A complete experimental matrix with mixtures of all possible concentrations (in steps of factors of 10) of PTS1 and Rh6G in the range of 1 nM to 0.1 mM was constructed. For each mixture, the lock-in response at 2 and 3 kHz was measured and plotted against dye concentration. The results are shown in FIGS. 7A and 7B. Each line represents a response with a particular background concentration of the other dye. This indicates the crosstalk between the dyes, or amount by which the background concentration of PTS1, for example, affects the measurement of the concentration of Rh6G.

G. Further Discussion

The lock-in measurements of the Rh6G dye response shows a slight DC level shift due to PTS1 concentration. As the concentration of PTS1 increases, the signal increases slightly. The PTS1 photo response curves for different level of Rh6G are similar with slight DC level shift. This is believed to be largely because of excitation light scattering by the other dye, which reduces the effective polarization filtering. Because the response is inherently non-linear, very small levels of additional response can lead to significant shift in the overall curve and change in apparent concentration.

Based on these results, it is believed that, with prior calibration and appropriate algorithms for mathematical fitting, with measurement of the response at both 2 and 3 kHz, the concentrations of Rh6G and PTS1 can be accurately determined. Further, this technique may be extended to different dyes or mixtures of more than two dyes.

This technique, which requires no color-dependent filters but distinguishes emission of two different dyes by color, can be easily extended to thin, lab-on-chip systems. Two integrated organic light sources combined with single organic photo detector and integrated polarizers would realize this system in a small, flat, disposable configuration. See, e.g., [7,8]. The system demonstrated good discrimination between two dyes to very low levels and detectability of 10 nM.

The present system and method may be used on a micromachined flow cytometry system, to classify fluorescently tagged cells as they pass through a small volume flow passage. Likewise, the system can be parallelized, to concurrently analyze a plurality of flow passages. In some cases, single illumination sources can be used for multiple flow passages. The flow cytometry system may be used, for example, to detect tumor cells. See, e.g., www.ivdiagnostics.com/about.html, www.purdue.edu/uns/x/2007b/070904LowPNAS.html, 2007 National Academy of Sciences paper: www.ncbi.nlm.nih.gov/pmc/articles/PMC1913863/, www.electroiq.com/index/display/nanotech-article-display/4553408772/articles/small-times/nanotechmems/mems/microfluidics/2010/september/lab-on-chip-project.html, each of which is expressly incorporated herein by reference.

Various aspect of the technology may be implemented on an automated computer using known components. The computer may be controlled in accordance with a tangible computer-readable medium, such as a magnetic disk, optical disk, flash memory, and other physical systems. The automated computer itself typically comprises a processor, which may be CISC, RISC, SIMD, or other types.

Embodiments hereof may be implemented as a method, apparatus, or article of manufacture using standard programming and/or engineering techniques to produce software, firmware, hardware, or any combination thereof to control a computer to implement the disclosed embodiments. The term "article of manufacture" (or alternatively, "computer program product") encompasses a computer program accessible from any computer-readable device, carrier, or media. For example, computer readable media can include but are not limited to magnetic storage devices (e.g., hard disk, floppy disk, magnetic strips, etc.), optical disks (e.g., compact disk (CD), digital versatile disk (DVD), BlueRay disks, etc.), smart cards, and flash memory devices (e.g., card, stick). Additionally it should be appreciated that various types of information can be communicated using a carrier wave such as those used in transmitting and receiving electronic mail or in accessing a network such as the Internet or a local area network (LAN). In some cases, these carrier waves reside within tangible media, and can be deemed non-transitory. Of course, those skilled in the art will recognize many modifications may be made to this configuration without departing from the scope or spirit of the disclosed embodiments.

Figure 8:
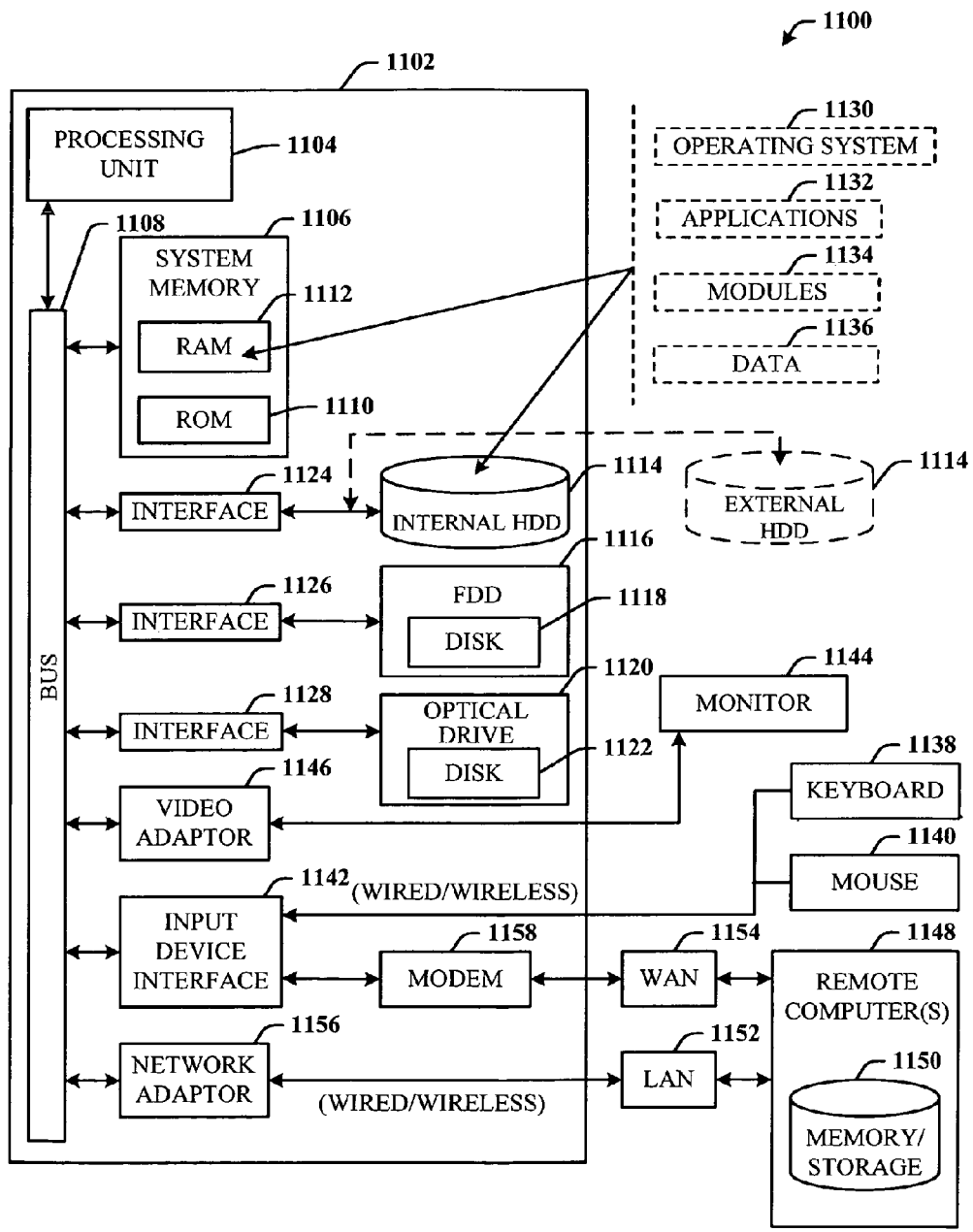
FIG. 8 shows a general computer architecture according to the prior art.

Referring now to FIG. 8, there is illustrated a block diagram of a computer operable to execute the disclosed architecture. In order to provide additional context for various aspects disclosed herein, FIG. 8 and the following discussion are intended to provide a brief, general description of a suitable computing environment 1100 in which the various aspects can be implemented. While the one or more embodiments have been described above in the general context of computer-executable instructions that may run on one or more computers, those skilled in the art will recognize that the various embodiments also can be implemented in combination with other program modules and/or as a combination of hardware and software.

Generally, program modules include routines, programs, components, data structures, etc., that perform particular tasks or implement particular abstract data types. Moreover, those skilled in the art will appreciate that the inventive methods can be practiced with other computer system configurations, including single-processor or multiprocessor computer systems, minicomputers, mainframe computers, as well as personal computers, hand-held computing devices, microprocessor-based or programmable consumer electronics, and the like, each of which can be operatively coupled to one or more associated devices.

The illustrated aspects may also be practiced in distributed computing environments where certain tasks are performed by remote processing devices that are linked through a communications network. In a distributed computing environment, program modules can be located in both local and remote memory storage devices.

A computer typically includes a variety of computer-readable media. Computer-readable media can be any available media that can be accessed by the computer and includes both volatile and nonvolatile media, removable and non-removable media. By way of example, and not limitation, computer-readable media can comprise computer storage media and communication media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital video disk (DVD) or other optical disk storage, magnetic cassettes, magnetic tape, magnetic disk storage or other magnetic storage devices, or any other medium which can be used to store the desired information and which can be accessed by the computer.

Communication media typically embodies computer-readable instructions, data structures, program modules or other data in a modulated data signal such as a carrier wave or other transport mechanism, and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer-readable media.

With reference again to FIG. 8, the exemplary environment 1100 for implementing various aspects includes a computer 1102, the computer 1102 including a processing unit 1104, a system memory 1106 and a system bus 1108. The system bus 1108 couples system components including, but not limited to, the system memory 1106 to the processing unit 1104. The processing unit 1104 can be any of various commercially available processors. Dual microprocessors and other multiprocessor architectures may also be employed as the processing unit 1104.

The system bus 1108 can be any of several types of bus structure that may further interconnect to a memory bus (with or without a memory controller), a peripheral bus, and a local bus using any of a variety of commercially available bus architectures. The system memory 1106 includes read-only memory (ROM) 1110 and random access memory (RAM) 1112. A basic input/output system (BIOS) is stored in a non-volatile memory 1110 such as ROM, EPROM, EEPROM, which BIOS contains the basic routines that help to transfer information between elements within the computer 1102, such as during start-up. The RAM 1112 can also include a high-speed RAM such as static RAM for caching data.

The computer 1102 further includes an internal hard disk drive (HDD) 1114 (e.g., EIDE, SATA), which internal hard disk drive 1114 may also be configured for external use in a suitable chassis (not shown), a magnetic floppy disk drive (FDD) 1116, (e.g., to read from or write to a removable diskette 1118) and an optical disk drive 1120, (e.g., reading a CD-ROM disk 1122 or, to read from or write to other high capacity optical media such as the DVD). The hard disk drive 1114, magnetic disk drive 1116 and optical disk drive 1120 can be connected to the system bus 1108 by a hard disk drive interface 1124, a magnetic disk drive interface 1126 and an optical drive interface 1128, respectively. The interface 1124 for external drive implementations includes at least one or both of Universal Serial Bus (USB) and IEEE 1394 interface technologies. Other external drive connection technologies are within contemplation of the one or more embodiments.

The drives and their associated computer-readable media provide nonvolatile storage of data, data structures, computer-executable instructions, and so forth. For the computer 1102, the drives and media accommodate the storage of any data in a suitable digital format. Although the description of computer-readable media above refers to a HDD, a removable magnetic diskette, and a removable optical media such as a CD or DVD, it should be appreciated by those skilled in the art that other types of media which are readable by a computer, such as magnetic hard drives, flash memory cards, optically readable media, and the like, may also be used in the exemplary operating environment, and further, that any such media may contain non-transitory computer-executable instructions for performing the methods disclosed herein.

A number of program modules can be stored in the drives and RAM 1112, including an operating system 1130, one or more application programs 1132, other program modules 1134 and program data 1136. All or portions of the operating system, applications, modules, and/or data can also be cached in the RAM 1112. It is appreciated that the various embodiments can be implemented with various available operating systems or combinations of operating systems.

A user can enter commands and information into the computer 1102 through one or more wired/wireless input devices, e.g., a keyboard 1138 and a pointing device, such as a mouse 1140. Other input devices (not shown) may include a microphone, a remote control, a joystick, a game pad, a stylus pen, touch screen, or the like. These and other input devices are often connected to the processing unit 1104 through an input device interface 1142 that is coupled to the system bus 1108, but can be connected by other interfaces, such as a parallel port, an IEEE 1394 serial port, a game port, a USB port, an interface, etc.

A monitor 1144 or other type of display device is also connected to the system bus 1108 through an interface, such as a video adapter 1146. In addition to the monitor 1144, a computer typically includes other peripheral output devices (not shown), such as speakers, printers, etc.

The computer 1102 may operate in a networked environment using logical connections through wired and/or wireless communications to one or more remote computers, such as a remote computer(s) 1148. The remote computer(s) 1148 can be a workstation, a server computer, a router, a personal computer, portable computer, microprocessor-based entertainment appliance, a peer device or other common network node, and typically includes many or all of the elements described relative to the computer 1102, although, for purposes of brevity, only a memory/storage device 1150 is illustrated. The logical connections depicted include wired/wireless connectivity to a local area network (LAN) 1152 and/or larger networks, e.g., a wide area network (WAN) 1154. Such LAN and WAN networking environments are commonplace in offices and companies, and facilitate enterprise-wide computer networks, such as intranets, all of which may connect to a global communications network, e.g., the Internet.

When used in a LAN networking environment, the computer 1102 is connected to the local network 1152 through a wired and/or wireless communication network interface or adapter 1156. The adaptor 1156 may facilitate wired or wireless communication to the LAN 1152, which may also include a wireless access point disposed thereon for communicating with the wireless adaptor 1156.

When used in a WAN networking environment, the computer 1102 can include a modem 1158, or is connected to a communications server on the WAN 1154, or has other means for establishing communications over the WAN 1154, such as by way of the Internet. The modem 1158, which can be internal or external and a wired or wireless device, is connected to the system bus 1108 through the serial port interface 1142. In a networked environment, program modules depicted relative to the computer 1102, or portions thereof, can be stored in the remote memory/storage device 1150. It will be appreciated that the network connections shown are exemplary and other means of establishing a communications link between the computers can be used.

The computer 1102 is operable to communicate with any wireless devices or entities operatively disposed in wireless communication, e.g., a printer, scanner, desktop and/or portable computer, portable data assistant, communications satellite, any piece of equipment or location associated with a wirelessly detectable tag (e.g., a kiosk, news stand, restroom), and telephone. This includes at least IEEE-802.11x (Wi-Fi), IEEE-802.15 (Bluetooth™), and IEEE-802.16 (WiMax) wireless technologies. Thus, the communication can be a predefined structure as with a conventional network or simply an ad hoc communication between at least two devices.

What has been described above includes examples of the various embodiments. It is, of course, not possible to describe every conceivable combination of components or methodologies for purposes of describing the various embodiments, but one of ordinary skill in the art may recognize that many further combinations and permutations are possible. Accordingly, the subject specification intended to embrace all such alterations, modifications, and variations that fall within the spirit and scope of the appended claims.

In particular and in regard to the various functions performed by the above described components, devices, circuits, systems and the like, the terms (including a reference to a "means") used to describe such components are intended to correspond, unless otherwise indicated, to any component which performs the specified function of the described component (e.g., a functional equivalent), even though not structurally equivalent to the disclosed structure, which performs the function in the herein illustrated exemplary aspects. In this regard, it will also be recognized that the various aspects include a system as well as a computer-readable medium having computer-executable instructions for performing the acts and/or events of the various methods.

In addition, while a particular feature may have been disclosed with respect to only one of several implementations, such feature may be combined with one or more other features of the other implementations as may be desired and advantageous for any given or particular application. Furthermore, to the extent that the terms "includes," and "including" and variants thereof are used in either the detailed description or the claims, these terms are intended to be inclusive in a manner similar to the term "comprising." See, U.S. Pat. No. 7,822,699, expressly incorporated herein by reference.

It should be understood that the various embodiments of the invention may be combined and subcombined in all possible consistent permutations. The scope of the invention is limited only by the claims, and no disclosed or preferred embodiment should be interpreted as limiting the generality of the invention.

REFERENCES

Each of the below references is expressly incorporated herein by reference.

[1] J. Khandurina, A. Guttman, "Bioanalysis in microfluidic devices", *J Chromatography A*., vol. 943, pp. 159-183, January 2002.
[2] J. R. Webster, M. A. Burns, D. T. Burke and C. H. Mastrangelo, "Monolithic capillary electrophoresis device with integrated fluorescence detector", *Anal. Chem.*, vol. 73, pp. 1622-1626, 2001.
[3] G. Kaigala, M. Behnam, A. Bidulock, C. Bargen, R. Johnstone, D. Elliot, C. Blackhouse, "A scalable and modular lab-on-a-chip genetic analysis instrument", *Analyst*, vol. 135, pp. 1606-1617, 2010.
[4] A. M. Jorgensen, K. B. Mogensen, J. P. Kutter, O. Geschke, "A biochemical microdevice with an integrated chemiluminescence detector", *Sensors and Actuators B*, vol. 90, pp. 15-21, 2003.
[5] Young-Hwan Kim, Kyeong-Sik Shin, Ji-Yoon Kang, Eun-Gyeong Yang, Kyeong-Kap Paek, Dae-Shik Seo, and Byeong-Kwon, "Poly(dimethylsiloxane)-Based Packaging Technique for Microchip Fluorescence Detection System Applications" *Journal of Microelectromechanical Systems*, vol. 15, pp. 1152-1158, 2006.
[6] M. L. Chabinyc, D. T. Chiu, J. C. McDonald, A. D. Stroock, J. F. Christian, A. M. Karger, and G. M. Whitesides, "An integrated fluorescence detection system in Poly (dimethylsiloxane) for Microfluidic Applications", *Anal. Chem.*, vol. 73, pp. 4491-4498, 2001.
[7] K. S. Shin, Y. H. Kim, K. K. Paek, J. H. Park, E. G. Yang, T. S. Kim, J. Y. Kang, B. K. Ju, "Characterization of an integrated fluorescence detection hybrid device with photodiode and organic light-emitting diode", *IEEE Electron Device Letters*, vol. 27, pp. 746-748, 2006.
[8] A. Pais, A. Banerjee, D. Klotzkin, and I. Papautsky, "High-sensitivity, disposable lab-on-a-chip with thin-film organic electronics for fluorescence detection," *Lab Chip*, vol. 8, pp. 794-800, 2008.
[9] E. Kraker, A. Haase, B. Lamprecht, G. Jakopic, C. Konrad, and Stefan Köstler, "Integrated organic electronic based optochemical sensors using polarization filters", *Appl. Phys. Lett.*, vol. 92, 033302, 2008.

What is claimed is:

1. A system configured for concurrently analyzing a sample for a presence of a plurality of analytes, comprising:
   a controllable optical source, configured to concurrently emit a plurality of independently controlled components of light having different optical characteristics;
   a control, configured to cause the controllable optical source to concurrently emit a plurality of respectively different amplitude modulated temporal patterns of the components of the light having different optical characteristics;
   a first polarizer having a first polarization, disposed within an optic path of an output of the controllable optical source;
   a sample space configured to contain the sample, illuminated by polarized light from the first polarizer;
   a second polarizer, having a second polarization different with respect to the first polarization, configured to receive light from the sample space, and to substantially pass scattered light from the sample space and to block light from the first polarizer having the first polarization;
   a sensor, configured to produce a signal corresponding to the scattered light passing through the second polarizer; and
   a lock-in detector, configured to receive an output from the sensor, and to coherently detect a respective signal component represented in the signal corresponding to a respective one of the plurality of independently controlled components, synchronized with the respectively different amplitude modulated pattern of the respective independently controlled component of the light, isolated from signal components corresponding to the other respective components of the light having respectively different amplitude modulated temporal patterns; and
   at least one processor configured to receive an output of the lock-in detector and to determine a concentration of at least one analyte in the sample based on at least a respective coherently detected signal component.

2. The system according to claim 1, wherein the different optical characteristics comprise a different spectral distribution, and the analyte comprises a plurality of different analytes, each optimally excited by a different optical wavelength of light, and producing a scattered optical emission selectively dependent on the intensity of illumination at an optimal wavelength of light.

3. The system according to claim 1, wherein the sample comprises a liquid or amorphous material.

4. The system according to claim 1, wherein the sensor has sufficient linearity to allow algorithmic separation and quantification of a respective concurrent plurality of different scattered optical emissions based on their respective different amplitude modulated temporal excitation patterns, wherein the plurality of respectively different amplitude modulated temporal patterns are orthogonal.

5. The system according to claim 1, wherein the sample comprises a fluorescent dye.

6. The system according to claim 1, wherein the sample comprises a plurality fluorescent dyes each having different optical absorption characteristics.

7. The system according to claim 6, wherein at least two of the plurality of dyes have overlapping spectral emission characteristics.

8. The system according to claim 1, wherein the respective different amplitude modulated temporal excitation patterns comprise different frequencies of amplitude modulation.

9. The system according to claim 1, wherein the respective different amplitude modulated temporal excitation patterns comprise different spread spectrum modulation patterns of optical intensity.

10. The system according to claim 9, wherein the spread spectrum modulation patterns comprise a direct sequence spread spectrum pattern.

11. The system according to claim 1, wherein an amplitude of an optical emission of the controllable optical source is adaptive to the output of the sensor.

12. The system according to claim 1, wherein the amplitude modulated temporal pattern of optical emission of the controllable optical source is adaptive to the output of the sensor.

13. The system according to claim 1, further comprising at least one transducer configured to measure an optical emission magnitude of the optical source.

14. The system according to claim 1, further comprising at least one transducer configured to separately measure an optical emission magnitude associated with each of the different optical characteristics.

15. The system according to claim 1, wherein the lock-in detector is further configured to detect, and the processor configured to determine, an optical scattering of a sample in the sample space which is independent of the concentration of the analyte.

16. The system according to claim 1, wherein the sensor is responsive to scattered light from the sample space substantially independent of a Stokes shift.

17. A method for concurrently measuring concentrations of a plurality of analytes in a sample, each displaying a different illumination-wavelength sensitive scattering, comprising:
illuminating a sample space with polarized illumination from a controllable optical source, configured to concurrently emit light having different respective optical characteristics having respectively different temporal optical emission amplitude patterns;
passing scattered light and polarized illumination from the sample space through a polarizer which blocks the polarized illumination and substantially passes the scattered illumination; and
receiving and analyzing the scattered light with a lock-in detector, to determine a concentration of the analyte in the sample based on a temporal analysis of the received scattered light synchronized with a respective temporal pattern of light having respective optical characteristics, to isolate signal components associated with the light having the respective optical characteristics and corresponding respective temporal optical emission amplitude pattern from concurrently emitted light having different optical characteristics and corresponding different temporal optical emission amplitude patterns.

18. The method according to claim 17, wherein the analyte comprises a plurality of different analytes, each optimally excited by a different optical wavelength of light, and producing a scattered optical emission selectively dependent on the intensity of illumination at an optimal wavelength of light.

19. The method according to claim 17 wherein the different temporal optical emission amplitude patterns are orthogonal, and the lock-in detector receives a signal from a sensor which has sufficient linearity to allow algorithmic separation and quantification of a respective concurrent plurality of different scattered optical emissions based on their respective different temporal amplitude emission patterns.

20. The method according to claim 17, wherein the sample comprises a plurality of different fluorescent dyes, each having distinct optical absorption characteristics and overlapping spectral emission characteristics.

21. The method according to claim 17, wherein the respective different temporal amplitude emission patterns comprise different frequencies of amplitude modulation.

22. The method according to claim 17, wherein the respective different temporal amplitude emission patterns comprise different direct sequence spread spectrum modulation patterns of optical intensity.

23. The method according to claim 17, further comprising adapting an amplitude of optical emission of at least one controllable optical source to an output of the lock-in detector.

24. A method for analyzing a sample for an analyte having an illumination-wavelength sensitive scattering, comprising:
illuminating a sample space with a plurality of different spectral characteristic, differently temporally amplitude modulated, polarized emission patterns;
detecting scattered light from the sample space while blocking polarized light from the polarized emission patterns; and
synchronously analyzing the detected scattered light with respect to the respective temporal amplitude modulation of the polarized emission patterns, to isolate emissions associated with each of the different spectral characteristics and quantify components of the detected scattered light corresponding to a respective spectral characteristic; and
outputting a signal in dependence on the synchronously analyzing.

25. An analyzer for detecting an illumination-wavelength sensitive scattering, comprising:
an illuminator subsystem configured to concurrently illuminate a sample space with a plurality of different sets of spectral characteristic, differently temporally amplitude modulated emission patterns;
a sensor configured to selectively detect scattered light from the sample space while blocking an effect of unscattered light from the emission patterns; and
a lock-in processor configured to coherently analyze an output of the sensor with respect to the a respective temporal amplitude modulation pattern, and to produce an output quantitatively dependent on components in the output of the sensor associated with a respective temporally amplitude modulated emission pattern isolated from components in the output of the sensor associated with respective different temporally amplitude modulated emission patterns.

26. The analyzer according to claim 25, wherein the plurality of different sets of spectral characteristic, differently temporally amplitude modulated emission patterns are polarized, and wherein the sensor is configured to block an effect of polarized light from the polarized emission patterns.

27. The analyzer according to claim 26, wherein the sensor is responsive to scattered light from the sample space in a manner substantially independent of a Stokes shift of the scattered light from a respective emission pattern.

* * * * *